(12) United States Patent
Yamazaki et al.

(10) Patent No.: US 9,709,388 B2
(45) Date of Patent: Jul. 18, 2017

(54) OPTICAL INNER SURFACE MEASURING DEVICE

(71) Applicant: NAMIKI SEIMITSU HOUSEKI KABUSHIKI KAISHA, Tokyo (JP)

(72) Inventors: Hiroshi Yamazaki, Kuroishi (JP); Eri Fukushima, Kuroishi (JP); Kazumi Yanagiura, Kuroishi (JP); Takafumi Asada, Kuroishi (JP)

(73) Assignee: Namiki Seimitsu Houseki Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/717,896

(22) Filed: May 20, 2015

(65) Prior Publication Data
US 2016/0341545 A1 Nov. 24, 2016

(51) Int. Cl.
*G01B 9/02* (2006.01)
*G01B 11/14* (2006.01)
(Continued)

(52) U.S. Cl.
CPC ............ *G01B 11/14* (2013.01); *G01B 9/0205* (2013.01); *G01B 9/02076* (2013.01);
(Continued)

(58) Field of Classification Search
CPC ...... G01B 9/02; G01B 11/002; G01B 11/026; G01D 5/266; G01D 5/38
(Continued)

(56) References Cited

U.S. PATENT DOCUMENTS

| 2005/0168751 A1* | 8/2005 | Horii | A61B 5/0062 356/479 |
|---|---|---|---|
| 2009/0079993 A1* | 3/2009 | Yatagai | A61B 5/0062 356/497 |

(Continued)

FOREIGN PATENT DOCUMENTS

| JP | H04-055504 U | 5/1992 |
|---|---|---|
| JP | H05-180627 A | 7/1993 |

(Continued)

OTHER PUBLICATIONS

The extended European search report issued by the European Patent Office on May 4, 2016, which corresponds to European Patent Application No. 15173406.8-1568 and is related to U.S. Appl. No. 14/717,896.

(Continued)

*Primary Examiner* — Tarifur Chowdhury
*Assistant Examiner* — Md M Rahman
(74) *Attorney, Agent, or Firm* — Studebaker & Brackett PC

(57) ABSTRACT

Higher-precision measurement is achieved by an optical inner surface measuring device configured to cause a probe to enter into the inner peripheral surface or deep hole of a target object, capture and observe reflection light from the inner surface in a three-dimensional manner, and measure the accuracy of the target object. In a structure including an optical fiber built into a tube, a light path conversion unit arranged at a leading end side of the optical fiber, and a motor configured to rotationally drive the light path conversion unit, a unit for measuring the amount of runout of a rotation shaft unit of the motor is provided. Shape data on the inner peripheral surface of a target object is obtained by calculating at a computer reflection light from the target object, and is modified by displacement amount data from a displacement measurement unit to realize high-precision measurement with no measurement error resulting from runout and rotational vibration of the rotation shaft of the motor.

8 Claims, 20 Drawing Sheets

(51) Int. Cl.
*G01B 11/12* (2006.01)
*G01B 11/24* (2006.01)
*A61B 1/00* (2006.01)
*G01B 11/30* (2006.01)

(52) U.S. Cl.
CPC .............. *G01B 11/12* (2013.01); *G01B 11/24* (2013.01); *A61B 1/00165* (2013.01); *A61B 1/00172* (2013.01); *G01B 11/2441* (2013.01); *G01B 11/30* (2013.01)

(58) Field of Classification Search
USPC ........................................................ 356/482
See application file for complete search history.

(56) References Cited

U.S. PATENT DOCUMENTS

| | | | |
|---|---|---|---|
| 2010/0268087 A1 | 10/2010 | Hirota | |
| 2012/0033324 A1* | 2/2012 | Muramatsu | G11B 19/2009 360/99.08 |
| 2013/0079644 A1* | 3/2013 | Peeters Weem | G02B 23/2423 600/476 |
| 2013/0096423 A1* | 4/2013 | Yamamoto | A61B 1/00006 600/424 |
| 2014/0323878 A1* | 10/2014 | Toriumi | G02B 21/0036 600/478 |
| 2015/0320318 A1 | 11/2015 | Yamazaki et al. | |

FOREIGN PATENT DOCUMENTS

| | | | |
|---|---|---|---|
| JP | 2000-321034 A | 11/2000 | |
| JP | 4461216 B2 | 5/2010 | |
| JP | 2014-130120 A | 7/2014 | |
| JP | 2014240670 A * | 12/2014 | ............ F16H 63/20 |
| WO | 2014/115361 A1 | 7/2014 | |

OTHER PUBLICATIONS

Lion Precision; "Shaft Runout Measurement with Noncontact Displacement Sensors"; Application Note; A05-0022; pp. 1-8; Jun. 2013.

* cited by examiner

OPTICAL INNER SURFACE MEASURING DEVICE

BACKGROUND

1. Technical Field

The present invention relates to an optical inner surface measuring device configured to cause a probe to enter into the inner peripheral surface or deep hole of a target object, radiate a light ray to the inner surface or deep hole bottom surface, capture and observe reflection light in a three-dimensional manner, and measure the dimension and geometric accuracy of the target object.

2. Description of the Related Art

For example, the finished dimension and geometric accuracy of a cylinder for an automobile engine significantly influence on power performance and fuel consumption efficiency of an automobile. These finished dimension and geometric accuracy are usually measured with the use of a contact measuring device such as a roundness measuring machine, a surface roughness meter, and a length measuring machine with a linear scale. In recent years, however, there has been provided an optical non-contact measuring device for the purpose of preventing a target object from being scratched.

As a means for observing the presence or absence of scratches on the inner surface of a target object in a non-contact manner, the image diagnostic technique (optical imaging technique) is widely used in manufacture of device machines and in medical practices. For example, as a method for investigating the depth of a deep hole and performing image diagnosis at sites of manufacturing precision equipment, in addition to camera observation with a general endoscope, a light ray is irradiated to capture reflection light by an optical sensor and automatically check for uneven brightness by a computer.

In the medical field, there have been studied and used techniques for observation of affected parts of a human body, such as X-ray CT, nuclear magnetic resonance, OCT imaging (optical coherence tomography) by an endoscope using coherence of light, all of which allow observation of tomographic images.

In the medical field, near infrared rays used as a light source reflect on the metallic inner peripheral surface of a deep hole in a target object, or pass partially through a resin film layer, if any, on the metallic inner surface of the same. Accordingly, it is possible to conduct at the same time three-dimensional shape observation of the inner peripheral surface, measurement of thickness accuracy of the film resin, and observation of a pin hole on the resin surface.

Typical structures of observation devices to which techniques for irradiating a light ray to the inner peripheral surface of a machine device or a machine component and observing or measuring the inner peripheral surface are described as in Japanese Patent No. 4461216, JP-UM-A-4-55504, and JP-A-5-180627, for example.

An optical endoscope probe described in Japanese Patent No. 4461216 is configured such that a reflection film (14) is provided at one end of a motor shaft (5) illustrated in FIG. 1 to radiate rotationally a light ray in 360 degrees. According to this configuration, however, an electric wire or wiring substrates (22) and (23) in a motor (1) block the rotationally radiated light ray, and thus the 360-degree radiation cannot be completely conducted to cause some portions from which no image data is captured.

An inner shape measuring sensor described in JP-UM-A-4-55504 is configured such that a hollow motor (26) provided at a leading edge side of a flexible tube (29) rotates a reflection mirror (20) to radiate a light ray as illustrated in FIG. 1. In addition, four strain gauges (5) illustrated in FIG. 4 measure the dimension (diameter) of the inner diameter of a target object in an XY direction, correct ambiguity in optical measurement values, and display the corrected dimension of the inner peripheral surface on a screen.

However, the requisite geometric accuracy of the inner shape of a target object is generally as high as about 0.05 µm. In this configuration, when the hollow motor (26) rotates at a high speed, the rotation shaft causes a large amount of runout or non-repeatable runout so as not to satisfy the requisite accuracy for the inner shape measurement sensor. Therefore, distortion or noise appears on the collected cross-section shape data of the inner peripheral surface of the target object, which disables acquisition of true measurement values.

An in-tube shape investigation device described in JP-A-5-180627 is configured such that the inside of a tube is spirally scanned with a light beam to obtain and display the inner diameter and three-dimensional shape data of the tube in a non-contact manner as illustrated in FIG. 10. However, JP-A-5-180627 does not propose a mechanism configured to radiate rotationally a light beam. Therefore, when the rotational motor for beam radiation rotates at a high speed, the rotation shaft causes runout or non-repeatable runout, and noise or distortion appears on the collected cross-section shape data of the inner peripheral surface of the target object, which disables acquisition of true measurement values.

SUMMARY

The present invention has been made in view of the foregoing circumstances. An object of the present invention is to provide an optical inner surface measuring device that allows correct and precise measurement of the inner diameter and accuracy measurement of the inner peripheral surface of a target object such that: a measurement probe is entered into the inner peripheral surface or deep hole bottom surface of the target object or an inner periphery of a long and bendable pipe; a light ray is rotationally radiated to the inner surface or the deep hole bottom surface; a reflected light ray is three-dimensionally collected and subjected to computer processing to obtain three-dimensional image data; the three-dimensional image data is observed to measure a dimension and geometric accuracy; distortion and vibration noise caused by runout or non-repeatable runout of a rotation shaft or a rotation unit rotationally radiating the light ray to the inner peripheral surface are removed from the image data.

A means for solving the foregoing problems is an optical inner surface measuring device configured to observe a target object and measure the dimension accuracy of the target object using an interference optical method (light interferometry, spectral interferometry, or the like), wherein the optical inner surface measuring device includes: an optical fiber built into a tube; at least one light path conversion unit arranged at a leading end side of the optical fiber; a motor configured to rotationally drive one or both of the optical fiber and the light path conversion unit; and a displacement detection unit configured to measure the amount of runout of a rotation shaft unit of the motor. According to this configuration, shape data of the inner peripheral surface of the target object, which obtained by calculating at a computer reflection light introduced from the target object through the optical fiber, is modified by displacement amount data in a runout detection unit.

According to the present invention, it is possible to remove image distortions or vibrations caused by runout or non-repeatable runout of the rotation shaft of the motor radiating rotationally the light ray, from the collected image data, thereby to realize correct and precise three-dimensional observation of the inner peripheral surface and high-accuracy measurement of the inner diameter and the inner peripheral surface.

DESCRIPTION OF THE EMBODIMENTS

Figure 1:
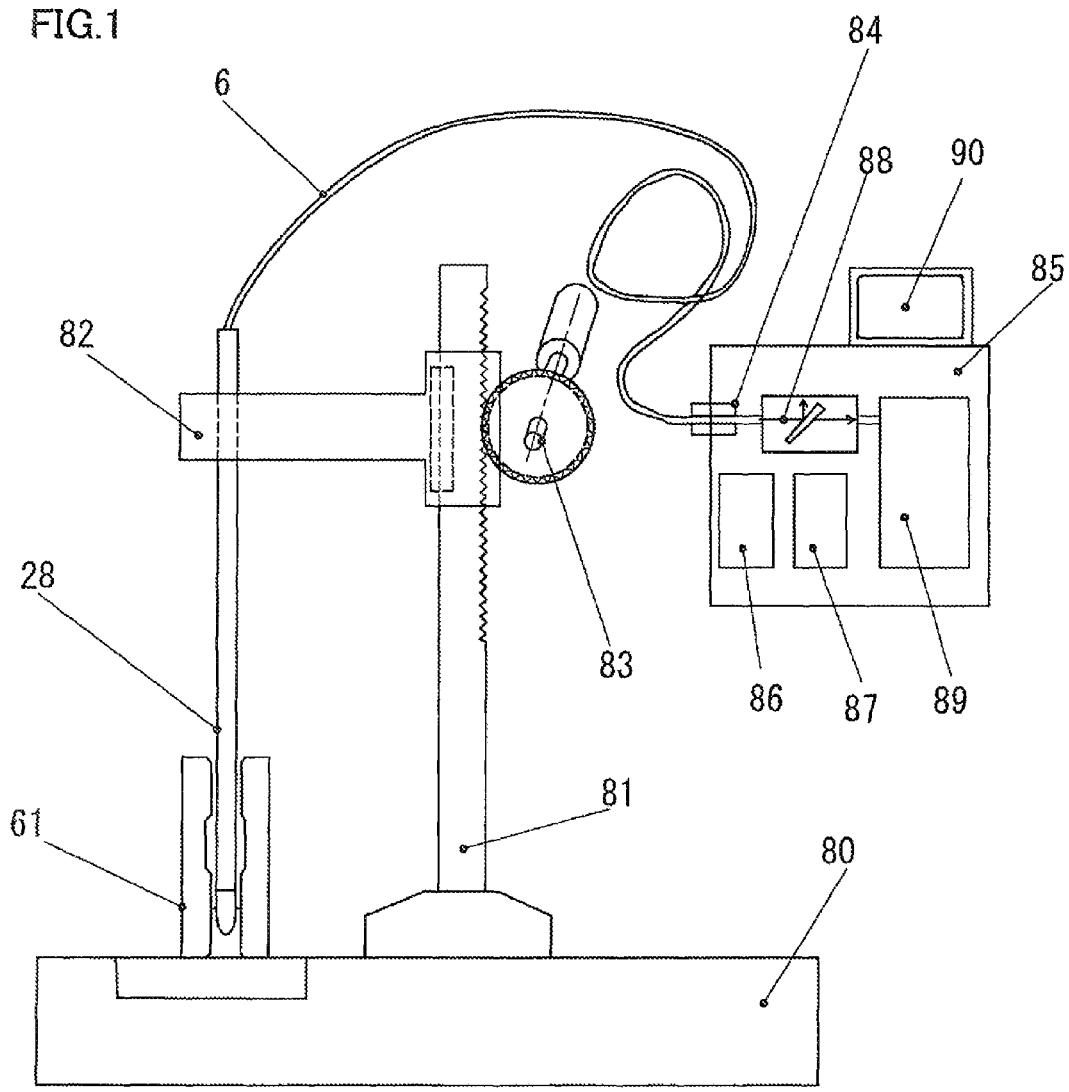
FIG. 1 is a diagram of an optical inner surface measuring device according to a first embodiment of the present invention.

A first feature of an optical inner surface measuring device configured to observe and measure a target object by optical interferometry in an embodiment is to include: an optical fiber built into a tube; at least one light path conversion unit arranged at a leading end side of the optical fiber; a motor configured to rotationally drive one or both of the optical fiber and the light path conversion unit; and a displacement detection unit configured to measure the amount of runout of a rotation shaft unit of the motor.

According to this configuration, measurement errors resulting from runout of the rotation unit can be modified by displacement amount data in a runout detection unit to realize high-accuracy observation and measurement.

As a second feature of the device, the displacement detection unit configured to measure the amount of runout of the rotation shaft unit of the motor is provided by arranging at least one runout detection sensor opposed to the outer peripheral surface of the rotation shaft unit of the motor.

According to this configuration, the runout detection sensor collects data on the amount of runout of the rotation shaft unit and modifies waveform data, thereby to realize correct and precise measurement of inner diameter and accuracy of the inner peripheral surface.

As a third feature of the device, reflection light from the target object obtained through the optical fiber is modified based on the shape data on the inner peripheral surface of the target object obtained by calculation at a computer and the displacement amount data from the displacement detection unit.

According to this configuration, it is possible to remove image distortions and vibrations resulting from runout and vibration of the rotation shaft unit from the original waveform data, thereby to realize more correct and precise measurement of inner diameter and accuracy of the inner peripheral surface.

As a fourth feature of the device, the displacement detection unit detects, as the amount of runout, a difference between reference shape data on the inner periphery of the tube and measurement data on the inner peripheral surface of the tube obtained during rotation of the rotation shaft.

According to this configuration, it is possible to remove image distortions and vibrations in the shape data on the inner peripheral surface of the target object from the collected waveform data, thereby to realize correct and precise measurement of inner diameter and accuracy of the inner peripheral surface.

As a fifth feature of the device, the bearing supporting the rotation shaft of the motor is provided by a dynamic-pressure bearing with a dynamic-pressure groove.

According to this configuration, the amount of runout, in particular, the amount of non-repeatable runout, of the rotation shaft of the motor decreases to reduce image distortions and vibrations in the shape data resulting from the runout of the rotation shaft, thereby to realize more precise measurement of inner diameter and accuracy of the inner peripheral surface.

As a sixth feature of the device, the rotation shaft unit of the motor has a hollow shape, the light path conversion unit is arranged so as to be rotatable integrally with the rotation shaft unit, and the optical fiber is inserted into a hollow of a rotation drive shaft so as to be rotatable relative to the rotation shaft unit.

According to this configuration, the rotation drive source is arranged in the vicinity of the light path conversion unit at the leading end side of the optical fiber built into the tube, and therefore the amount of runout, in particular, the amount of non-repeatable runout, of the rotation shaft decreases to reduce image distortions and vibrations in the shape data resulting from the runout of the rotation shaft, thereby to realize more precise measurement of inner diameter and accuracy of the inner peripheral surface.

As a seventh feature of the device, the motor includes a first motor and a second motor arranged behind the first motor, and the light path conversion unit includes a first light path conversion unit operated by the first motor and a second light path conversion unit operated by the second motor. In addition, the optical fiber includes a fixation-side optical fiber arranged non-rotatably in the tube via a fixture behind the second motor and a rotation-side optical fiber rotating integrally with the rotation shaft unit of the first motor or the second motor. Each of the rotation shaft units of the first motor and the second motor has a hollow shape. At least part of the rotation-side optical fiber at the leading end side is inserted into the hollow of the rotation shaft unit of the first motor, and at least part of the same at the back side is fixed to the hollow of the rotation shaft unit of the second motor. The first light path conversion unit is arranged at the leading end side of the second light path conversion unit so as to be rotatable integrally with the rotation shaft unit of the first motor, and the second light path conversion unit is provided at the leading end of the rotation-side optical fiber.

According to this configuration, there are no wires of the first and second motors within the range of scanning with a radiated light ray in a three-dimensional manner, and therefore no shadow is casted on the light ray to realize high-precision measurement without loss in the collected data.

As an eighth feature of the device, the first light path conversion unit described in particular in relation to the seventh feature is a rotatable mirror or prism.

According to this configuration, it is possible to realize high-precision accuracy measurement with higher reflection efficiency and lower optical loss.

As a ninth feature of the device, the second light path conversion unit described in particular in the seventh feature is a prism with an almost flat plane inclined toward the leading end.

According to this configuration, it is possible to realize high-precision accuracy measurement with higher light collection efficiency and lower optical loss.

As a tenth feature of the device, the rotation shaft unit of the motor has a hollow shape, and the optical fiber is inserted into the hollow of the rotation shaft so as to be rotatable relative to the rotation shaft. The motor has a hollow slide shaft unit extended backward, and a direct-acting actuator using the slide shaft unit as an output axis is provided. The optical fiber is fixed to the hollow of the slide shaft unit. In this structure, the output shaft of the direct-acting actuator presses and pulls the optical fiber, and at the same time, slides axially the light path conversion unit, the motor, and the optical fiber in the vicinity of the leading end side.

According to this configuration, it is possible to radiate a light ray in a three-dimensional manner by operations of the motor and the direct-acting motor and collect three-dimensional shape data. Accordingly, there are no wires of the first motor and the direct-acting motor within the range of scanning with a light ray, and therefore no shadow is casted on the light ray to realize high-precision measurement without loss in the collected data.

Next, preferred embodiments of the present invention will be described with reference to the accompanying drawings.

EXAMPLE 1

A first embodiment of the optical inner surface measuring device according to the present invention will be described. FIGS. 1 to 10 illustrate the embodiment of the optical inner surface measuring device according to the present invention.

FIG. 1 illustrates an optical inner surface measuring device according to the first embodiment of the present invention. A stand 81 is fixed to a base 80, and a slider 82 and a probe 28 are vertically moved by a slider motor 83. A target object 61 is set on the base 80, and the probe 28, 58 comes in and out of a deep hole 61a in the target object 61 illustrated in FIG. 2. A light ray having entered into the probe 28, 59 passes through a tube 6 and a connection unit 84 of a measuring machine main body 85, and enters into an optical interference analysis unit 88. The light ray is then analyzed by a computer 89, and an image is displayed on a monitor 90.

Figure 2:
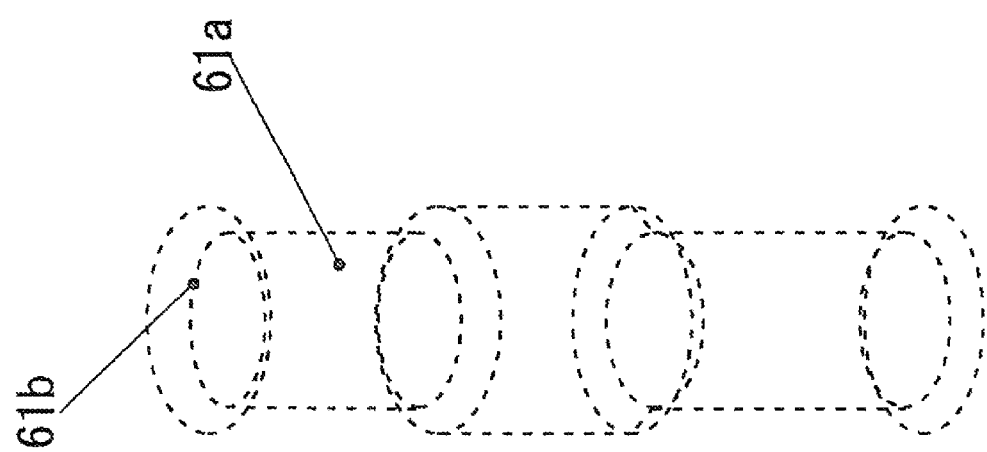
FIG. 2 is a three-dimensional diagram of an inner shape of a target object at the optical inner surface measuring device.
Figure 3:
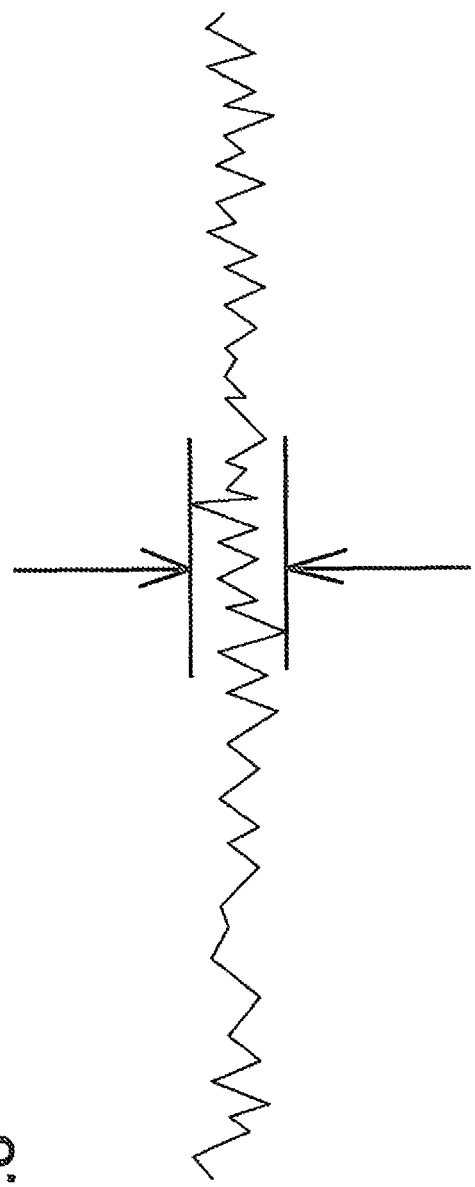
FIG. 3 is a diagram describing surface roughness at the optical inner surface measuring device.
Figure 4:
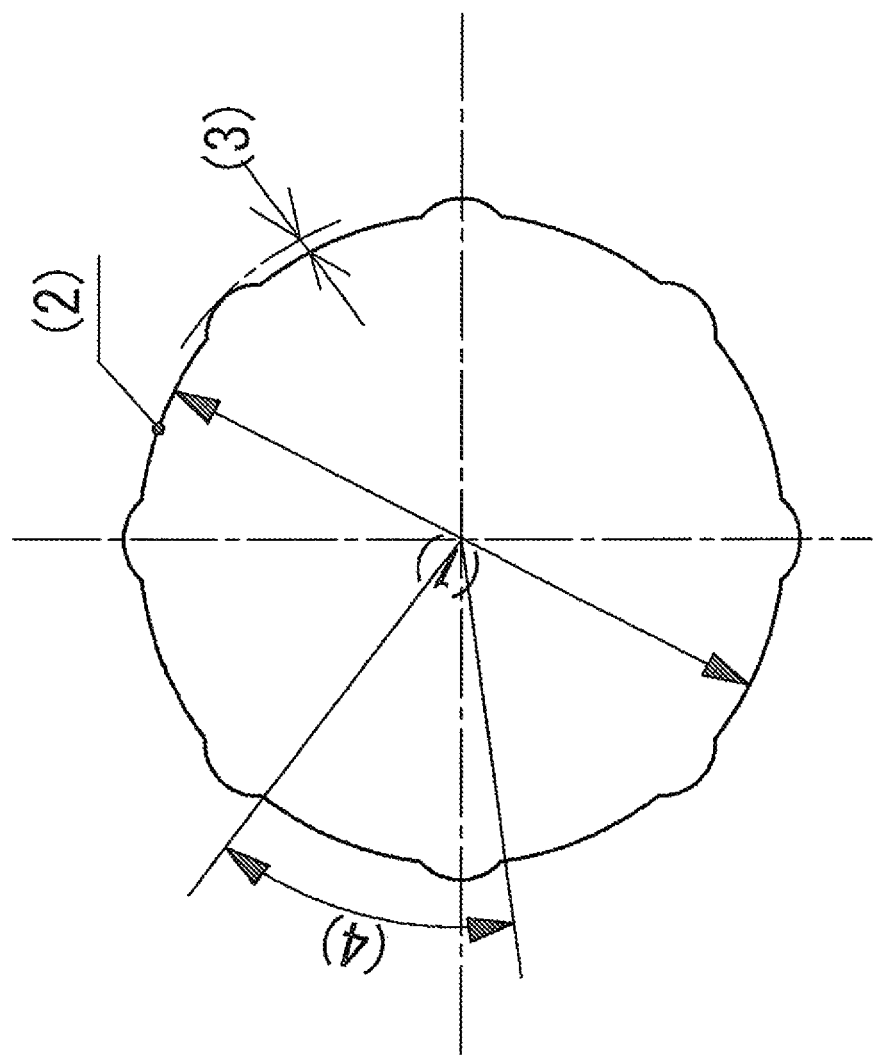
FIG. 4 is a diagram describing geometric accuracy of the optical inner surface measuring device.

The optical inner surface measuring device has more than one, for example, eight functions as follows:

[A] Function to display a three-dimensional shape of inner surface of the deep hole 61a illustrated in FIG. 2 and perform appearance inspection for burrs, scratches, and others;

[B] Function to, if applicable, measure the film thickness of a surface film 61b of resin or the like on the inner peripheral surface of the deep hole 61a, and perform inspection for pin hole failure and undesired projections;

[C] Function to measure surface roughness as illustrated in FIG. 3;

[D] Function to measure diameter as illustrated in FIG. 4 (1);

[E] Function to measure roundness as illustrated in FIG. 4 (2);

[F] Function to measure cylindricity by which to collect successively roundness measurement data in FIG. 4 (2) in a longitudinal direction and display the same in a three-dimensional manner;

[G] Function to measure the height of an asperity on the inner peripheral surface as illustrated in FIG. 4 (3); and

[H] Function to measure an angle pitch as illustrated in FIG. 4 (4).

Figure 5:
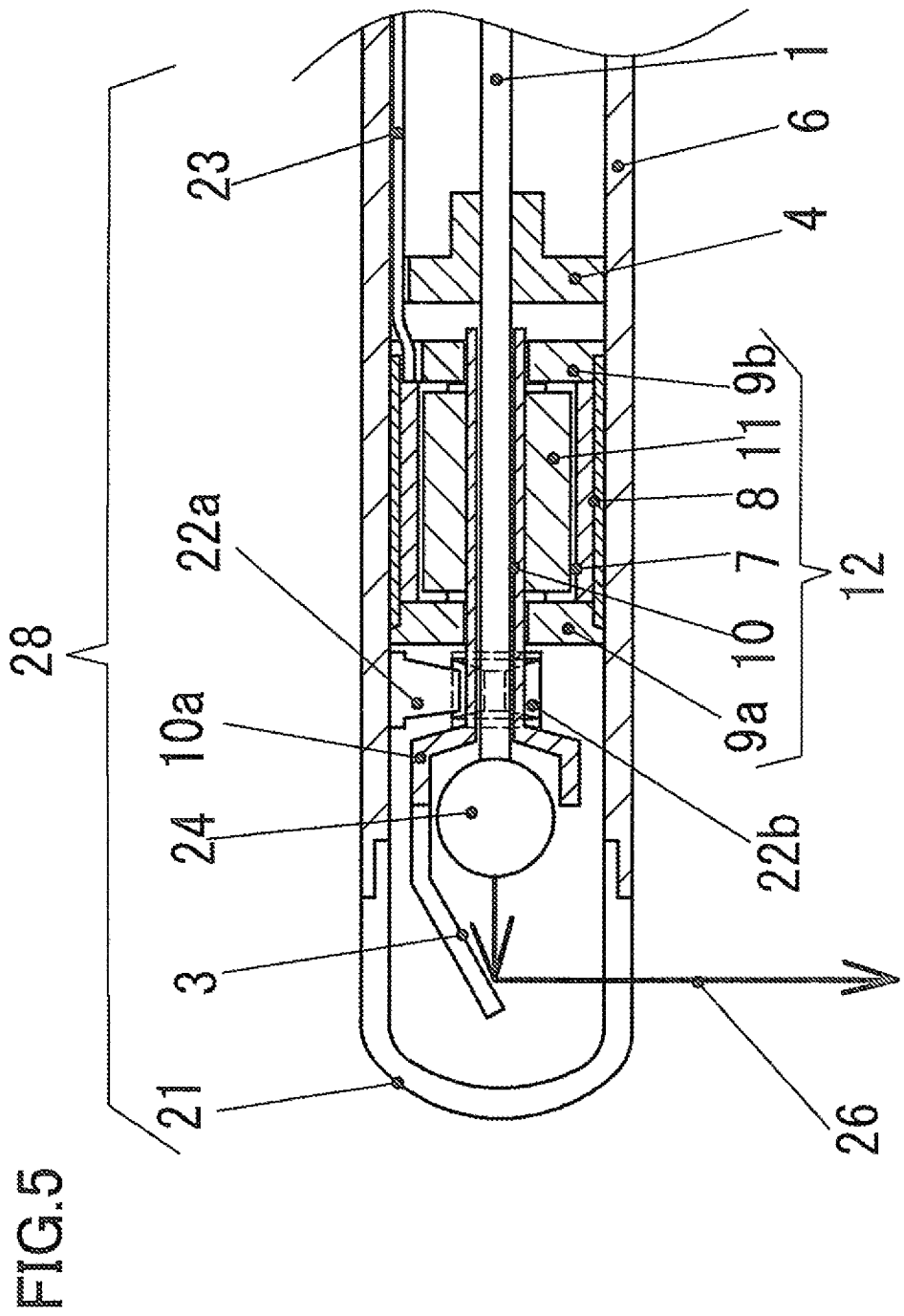
FIG. 5 is a configuration diagram of a probe unit of the optical inner surface measuring device.

FIG. 5 is a configuration diagram of the probe unit 28 of the optical inner surface measuring device according to the first embodiment of the present invention. The probe unit 28 has an optical fiber 1 connected at the leading end side and the back side in the tube 6 and fixed by an optical fiber fixture 4, and has a light-collecting lens 24 such as a ball lens integrated with the leading end side of the optical fiber 1. The probe unit 28 also has a motor 12 with a hollow rotation shaft 10 arranged almost coaxially with the fixation-side optical fiber 1 in the vicinity of the leading end of the fixation-side optical fiber 1.

The fixation-side optical fiber 1 is inserted into the hollow rotation shaft 10 so as to be relatively rotatable. A first light path conversion unit 3 is formed from a mirror or a prism, for example, is attached and rotated at the leading end side of a holder portion 10a extended from the leading end side of the hollow rotation shaft 10 across the light-collecting lens 24.

Figure 7:
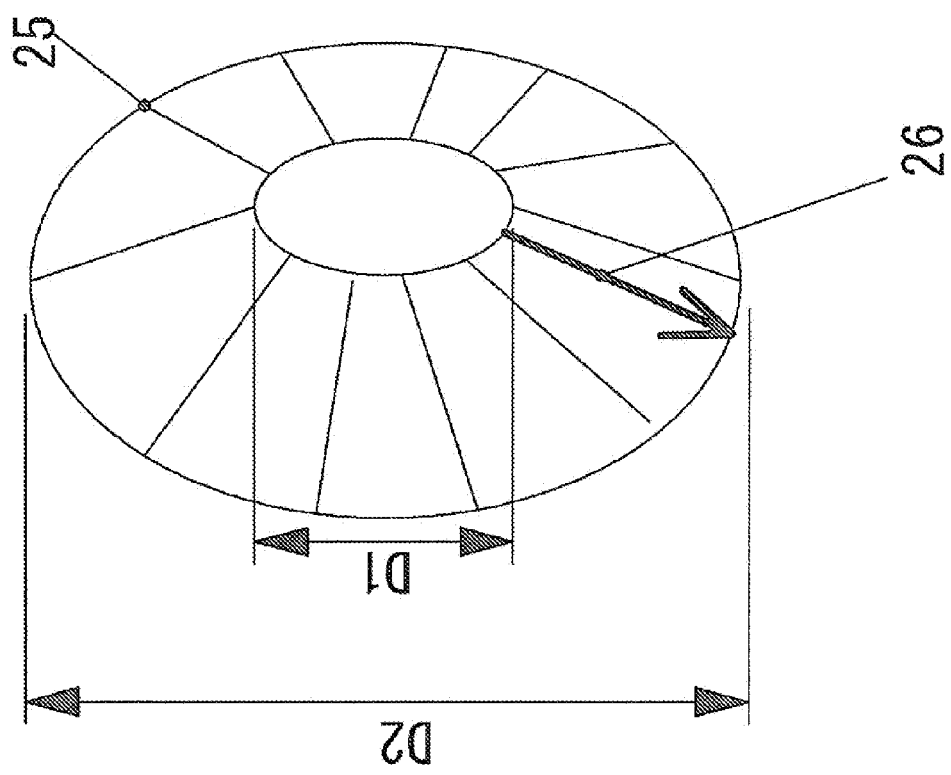
FIG. 7 is a diagram describing a scan range of the optical inner surface measuring device.

Light ray 26, 27 from the back side of the fixation-side optical fiber 1 having passed through the light-collecting lens 24 is reflected at an angle relative to a shaft center line. The light ray 26, 27 then passes through a light passage unit of the transparent member 21 and is applied to the deep hole 61a of the target object 61. At that time, the light ray 26, 27 is radiated in 360 degrees as illustrated in FIG. 7. In FIG. 7, reference sign D1 denotes the outer diameter of the transparent member 21. The light ray 26, 27 is radiated within the range of radiuses 2 to 10 mm indicated with reference sign D2 in FIG. 7, and reflection light is collected.

Since the slider motor 83 illustrated in FIG. 1 moves the probe 28 in the axial direction of the deep hole 61a and the light ray 26 is rotationally radiated and axially slid. This makes it possible to radiate the light ray to the entire deep hole 61a illustrated in FIG. 2 and collect three-dimensional shape data.

In the first embodiment illustrated in FIG. 5, the axial movement of the light ray 26 is not programmed in the probe 28 but is performed by the external slider motor 83 illustrated in FIG. 1. Accordingly, the accuracy of straight-ahead movement of the slider 82 is as high as 0.1 µm.

The motor 12 includes a motor case 8, bearings 9a and 9b, a motor coil 7, a rotor magnet 11 fixed to the hollow rotation shaft 10. The motor 12 is rotated with power supply from an electric wire 23. A first motor driver circuit 86 supplies power to the motor 12. A three-dimensional image produced by analyzing data at the computer 89 is displayed on the monitor 90.

Figure 6:
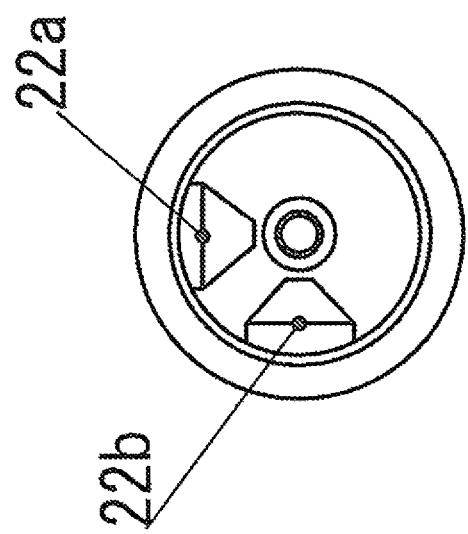
FIG. 6 is a cross-sectional view of the probe unit of the optical inner surface measuring device.

Referring to FIGS. 5 and 6, two runout detection sensors 22a and 22b detect the amount of runout of the outer peripheral surface of the rotating hollow rotation shaft 10 and the angular direction of the runout. The runout detection sensors detect changes in statistic capacity and reflection light resulting from the runout of the hollow rotation shaft 10, convert the changes into displacement amount, and take in the converted data.

The foregoing eight measurement methods practiced by the optical inner surface measuring device of the present invention and operations of the eight methods will be described below in sequence.

[A] Method of display of a three-dimensional shape and appearance inspection for the presence or absence of scratches and the like Reflection light from the deep hole 61a of the target object 61 illustrated in FIG. 1 is taken into the optical interference analysis unit 88 and calculated by the computer 89, and then an image with the same shape as that illustrated in FIG. 2 is displayed. The slider motor 83 takes in the reflection light in a three-dimensional manner while sliding the probe 28 in the axial direction, so that a three-dimensional image can be displayed on the monitor 90. According to the present invention, it is possible to observe a high-solution and clear three-dimensional image of the inner peripheral surface which could not obtained by conventional CCD cameras or ultrasound sensor systems.

In addition, poor-appearance articles can be detected by storing in advance reference data on a target object without burrs or scratches in a memory and comparing the taken actual surface state of the target object 61 to the reference data.

[B] Next, when the inner peripheral surface of the deep hole 61a is covered with a film coating of resin or the like, the resin is semi-permeable to a near infrared ray or laser light. Accordingly, concerning the measurement of the thickness of a surface layer 61b and check for pin hole failure or undesired projections, it is possible to obtain a high-resolution three-dimensional image of the target object with the film and measure the thickness of the film.

Figure 8:
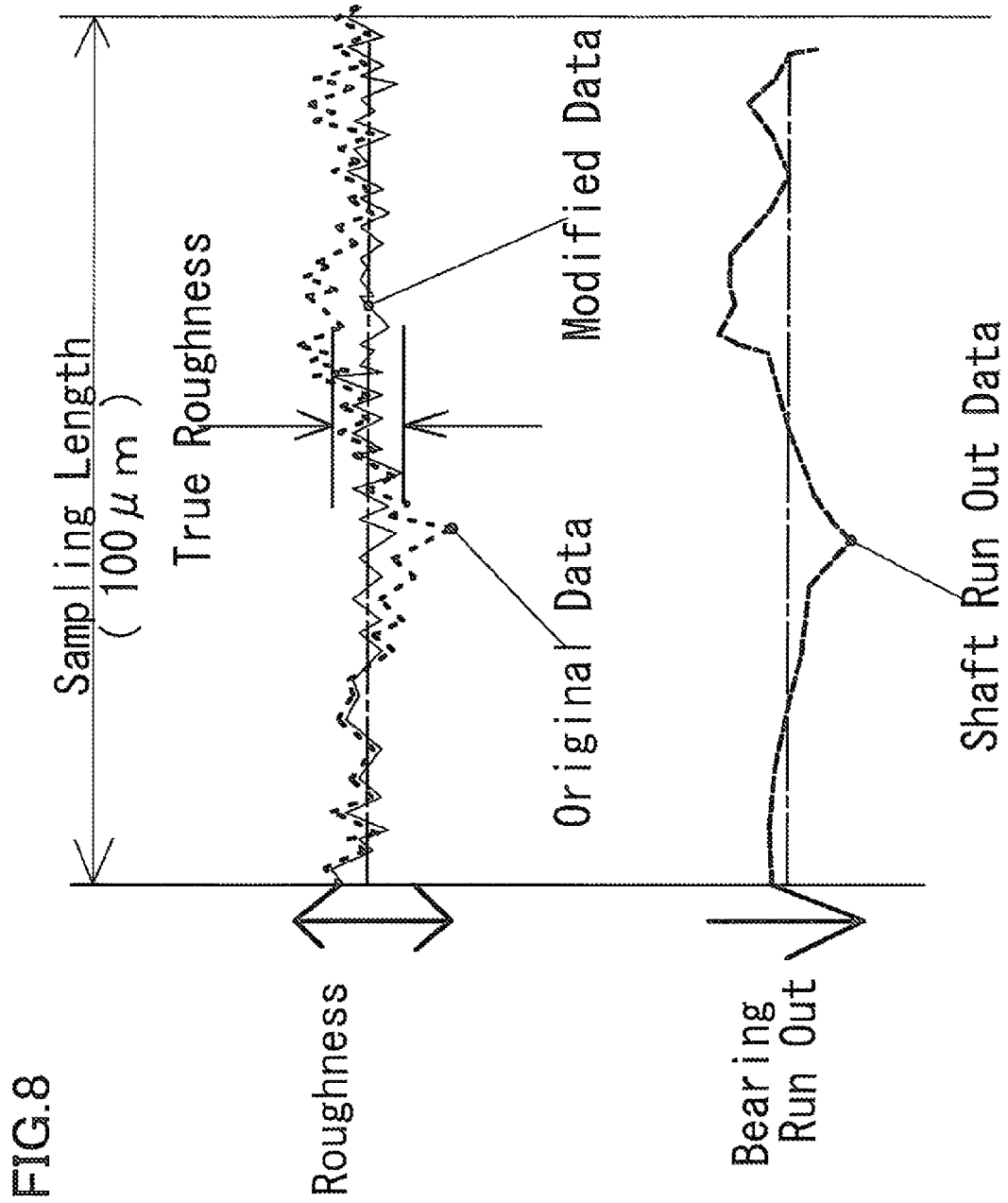
FIG. 8 is a diagram describing a surface roughness correction method of the optical inner surface measuring device.

[C] According to the surface roughness measurement method, as illustrated in FIG. 8, original waveform data (waveform indicated by a broken line at the upper side of FIG. 8) on the inner peripheral surface of the target object 61 within the range of sampling length (for example, 100 µm) is collected, and at the same time, shaft runout waveform data (waveform at the lower side of FIG. 8) obtained by the runout detection unit (sensors 22a and 22b in FIG. 5) taking in outer periphery runout of the hollow rotation shaft 10 is collected, and the shaft runout data is subtracted from the original waveform data to obtain modified data (waveform indicated by a thin solid line at the upper side of FIG. 8). The difference between the maximum value and minimum value of the modified data constitutes a true maximum surface roughness value. As described above, high-precision surface roughness measurement is allowed by obtaining and modifying the outer periphery runout data of the hollow rotation shaft 10.

Figure 9:
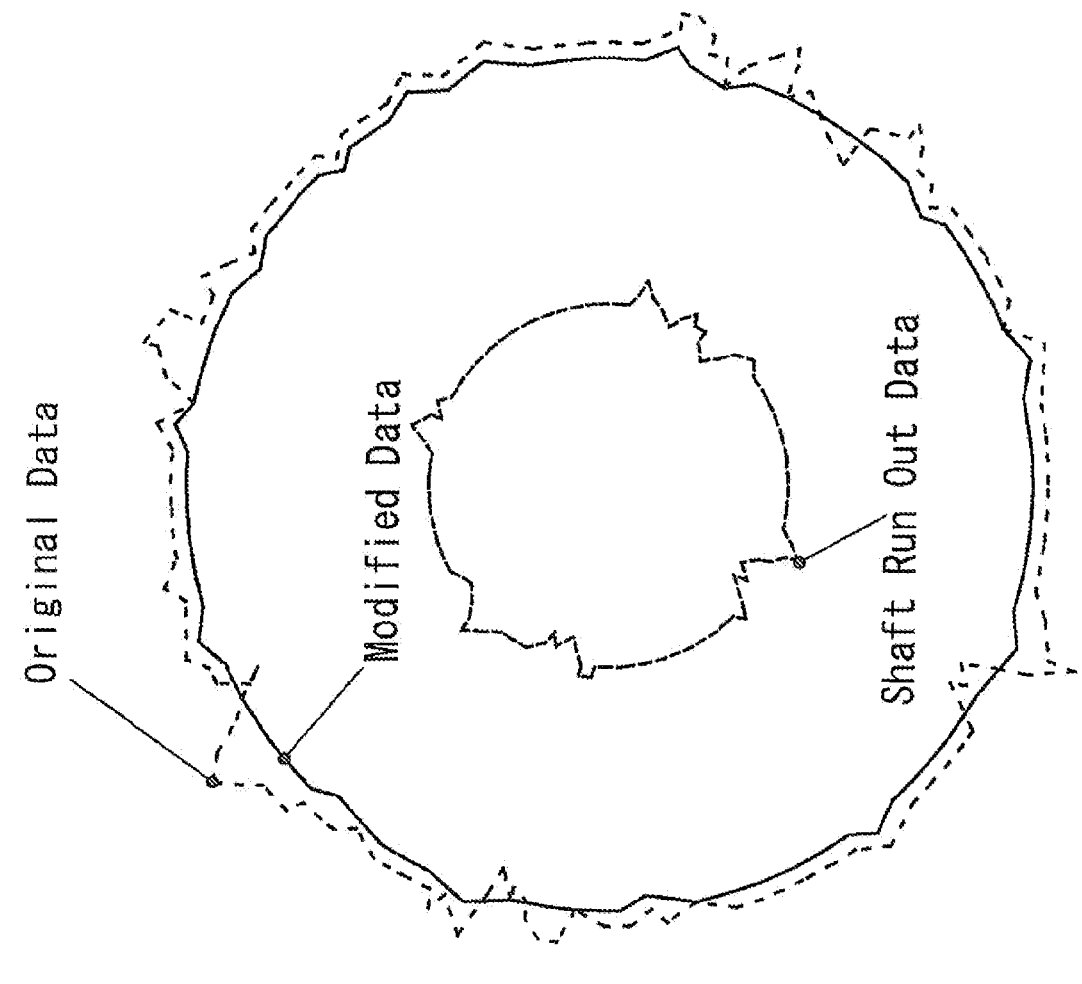
FIG. 9 is a diagram describing a roundness correction method of the optical inner surface measuring device.

[D] The diameter measurement method is practiced as described below. The waveform indicated by a broken line on the outer side in FIG. 9 is an original waveform indicating of the shape of the inner peripheral surface of the target object 61 obtained by calculating at the computer 89 reflection of light radiated from the first light path conversion unit 3 in 360 degrees. The shaft runout displacement data obtained from the runout detection unit (sensors 22a and 22b in FIG. 5) indicated by a thick solid-line waveform on the inner side in FIG. 9 is subtracted from the original waveform to obtain modified data indicated by a thin solid line on the outer side in FIG. 9. The modified data can be used to obtain the desired inner diameter.

[E] According to the roundness measurement method, the thin solid line on the outer side in FIG. 9 described above indicates the modified data, an inscribed circle and a circumscribed circle relative to the modified data are calculated, and the difference in radius between the two circles is defined as roundness.

[F] According to the cylindricity measurement method, the slider motor 83 slides the probe 28 together with the slider 82 at a high linearity accuracy of 0.1 µm or less, roundness measurement data is successively collected in the longitudinal direction to obtain a three-dimensional image of a cylinder, and the difference in radius between an inscribed cylinder and a circumscribed cylinder in the image is defined as cylindricity.

[G] The measurement method for asperity height on the inner peripheral surface is used to measure the depth of a dynamic-pressure groove formed in the inner peripheral surface of a dynamic-pressure bearing, for example. The measurement method is practiced in the same manner as the surface roughness measurement method described above.

Figure 10:
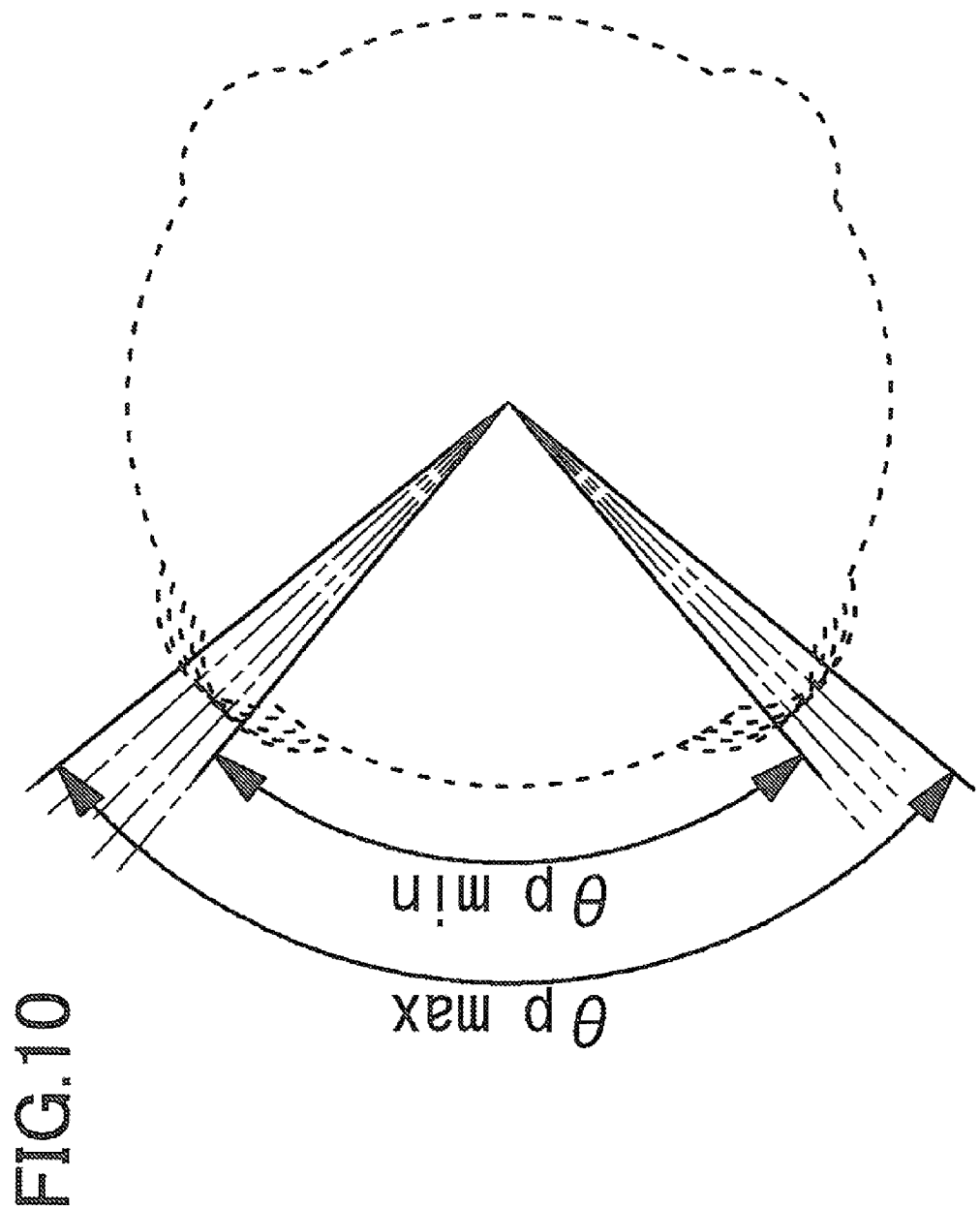
FIG. 10 is a diagram describing an angle pitch correction method of the optical inner surface measuring device.

[H] When the first motor 12 rotates the first light path conversion unit 3, unevenness occurs in the rotation speed (called jitter or wow and flutter) of the first motor 12 to cause variations in measurement value of a true angle θ illustrated in FIG. 10 in the range between a maximum θpmax and a minimum θpmin. Accordingly, it is necessary to solve the problem by the angle pitch measurement method to measure repeatedly the angle a sufficient number of times and average the measurement values by a computer to obtain a true value.

Referring to FIG. 5, the runout of the outer peripheral surface of the rotating hollow rotation shaft 10 is generally about 1 µm. The runout can be divided into repeatable runout that occurs once per revolution and non-repeatable runout that occurs at varied frequencies in a wide range from low to high frequencies The first bearing 9a varies in design and type. For example, when the first bearing 9a is a ball bearing, rolling vibration of the ball causes a large amount of non-repeatable runout. Meanwhile, when the first bearing is an oil-impregnated sintered bearing, whirling vibration and contact surface vibration cause a large amount of non-repeatable runout.

Figure 11:
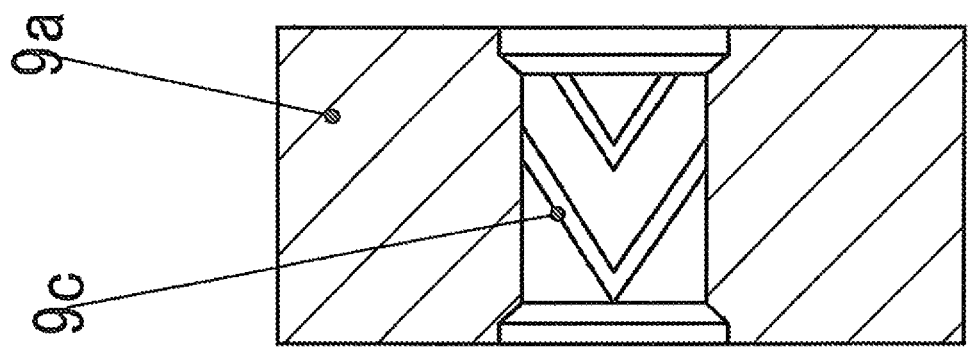
FIG. 11 is a cross-sectional view of a dynamic pressure bearing of the optical inner surface measuring device.

In this example, as illustrated in FIG. 11, the dynamic-pressure bearing 9a includes a dynamic-pressure generating groove 9c on the inner peripheral surface. Upon rotation of the dynamic-pressure bearing 9a, the dynamic pressure generating groove 9c provides a pumping force to a lubricant fluid such as an oil, so that the rotation shaft is lifted and rotated at a high accuracy in a non-contact manner.

Accordingly, the bearing in this example has no rolling vibration caused by conventional ball bearings or whirling or friction caused by conventional oil-impregnated sintered bearings, and therefore causes a very small amount of non-repeatable runout. As a result, when the original data illustrated in FIGS. 8 and 9 is modified by subtraction of the shaft runout data, the shaft runout data is provided as a smooth waveform to modify the original data at a high accuracy, thereby resulting in further increase of measurement accuracy.

Referring to FIGS. 5 and 6, the displacement detection unit for measuring the amount of runout of the rotation shaft unit of the first motor has the plurality of runout detection sensors 22a and 22b opposed to each other on the outer peripheral surface of the first hollow rotation shaft. Alternatively, the displacement detection unit may be configured in other manners.

For example, another displacement detection unit for measuring the amount of runout of the rotation shaft unit of the first motor 12 is configured to detect the difference between reference shape data on the inner periphery of the tube 6 stored in advance in a memory and actual measurement data of the inner peripheral surface of the tube obtained during rotation of the first motor. In this case, FIG. 9 indicates by an inside solid line the data on the amount of runout determined from the difference between the reference shape data on the inner peripheral surface of the tube and the measurement data obtained during rotation of the first motor. According to this configuration and detection method, it is also possible to remove image distortion and vibration in the shape data on the inner peripheral surface of the target object from the collected waveform data, and realize correct and high-precision measurement of inner diameter and accuracy of the inner peripheral surface. The tube 6 is formed from a glass or a transparent resin. The inner peripheral surface of the tube 6 may have as appropriate a light-permeable metal coating with a thickness of several nanometers, so that the outline of the inner peripheral surface can be detected more reliably by the collected waveforms from the inner peripheral surface.

Figure 19:
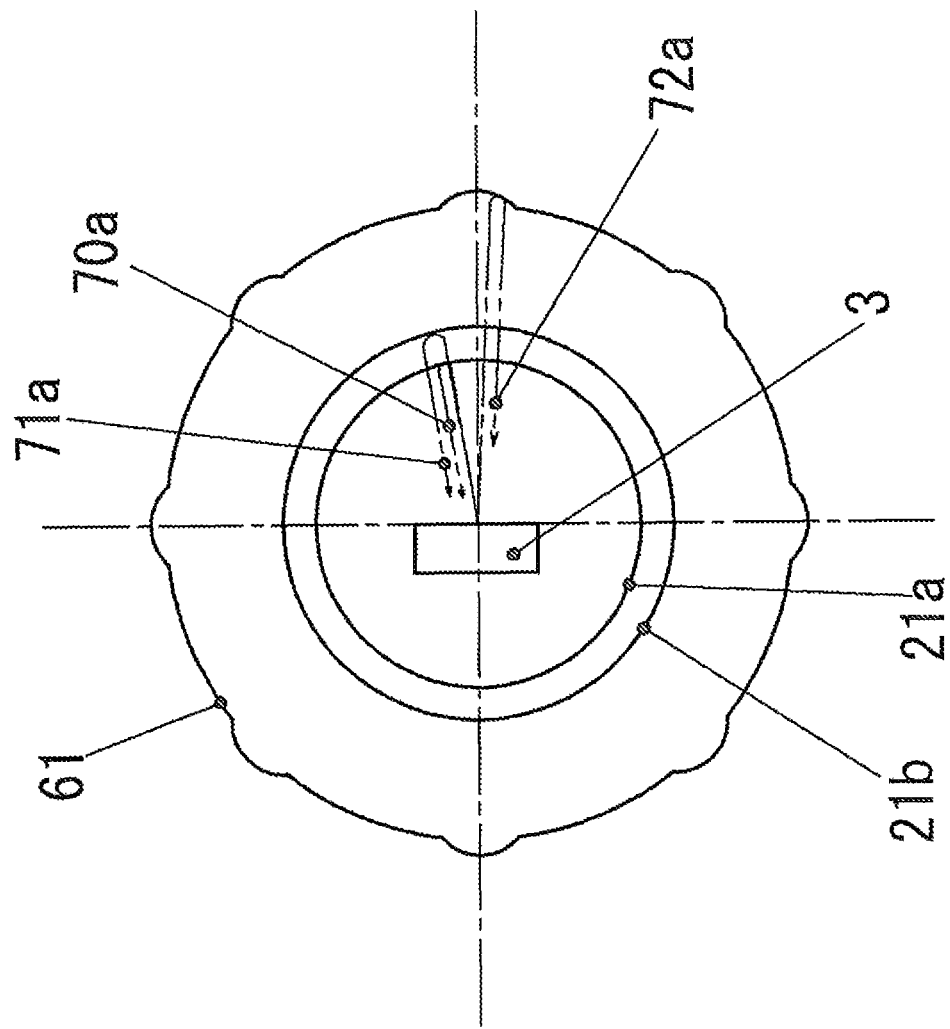
FIG. 19 is a cross-sectional view of the optical inner surface measuring device according to the first embodiment of the present invention.
Figure 20:
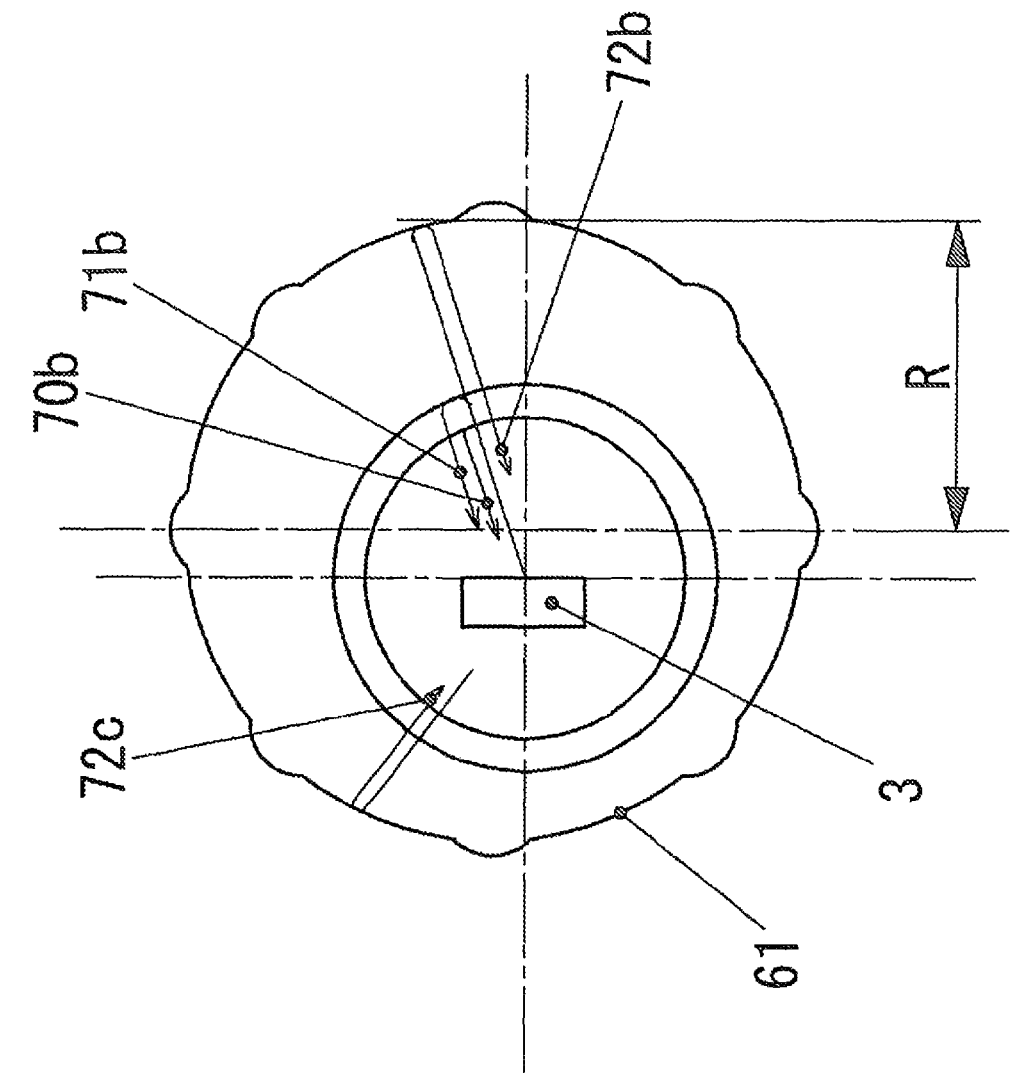
FIG. 20 is a cross-sectional view of the optical inner surface measuring device.

FIGS. 19 and 20 are cross-sectional views of the optical inner surface measuring device according to the first embodiment of the present invention. Light ray emitted from the first light path conversion unit 3 (rotating mirror) is reflected on an inner peripheral surface 21a and an outer peripheral surface 21b of the transparent member 21 and the target object 61, and the reflection light is returned to the fixation-side optical fiber 1 through the first light path conversion unit.

At that time, 360-degree shape data taken in from either of the inner peripheral surface 21a and the outer peripheral surface 21b of the transparent member corresponds to the amount of runout of the first light path conversion unit 3 at the inner side of the double shape data illustrated in FIG. 9. This measurement makes it possible to remove image distortion and vibration in the shape data on the inner peripheral surface of the target object from the collected waveform data, or correct the image distortion and vibration.

The position of the probe 28 including the transparent member 21 in the target object is shifted between FIGS. 19 and 20. The measurement of the inner shape can be performed without problem even when the first light path conversion unit takes in 360-degree shape data while rotating.

The tube 6 has a diameter of about 2 mm. The fixation-side optical fiber 1 penetrating through the tube 6 is a bendable glass fiber and has a diameter of about 0.1 to 0.4 mm.

The first light path conversion unit 3 illustrated in FIG. 1 is formed from a mirror or a prism with a smooth reflection surface. To increase a reflection ratio, the first light path conversion unit 3 is polished with surface roughness and flatness equal to or higher than those of general optical components.

The first hollow rotation shaft 10 illustrated in FIG. 1 is formed from metal or ceramic. The first hollow rotation shaft 10 is formed hollow by a drawing process in which a weld metal is drawn from a die or by an extrusion process in which ceramic before burning is extruded from a die, and, after hardening treatment, is finished by a polishing process.

Referring to FIG. 1, the hole of the first hollow rotation shaft 10 has a diameter of 0.2 to 0.5 mm that is sufficiently larger than the diameter of the optical fiber 1. Accordingly, the fixation-side optical fiber 1 fixed by the fixture 4 hardly contacts the first hollow rotation shaft 10. Even if the fixation-side optical fiber 1 slightly contacts the first hollow rotation shaft 10, no abrasion power is generated or no variation occurs in rotational friction torque.

EXAMPLE 2

FIGS. 12 to 16 illustrate a second embodiment of an optical inner surface measuring device according to the present invention.

Figure 12:
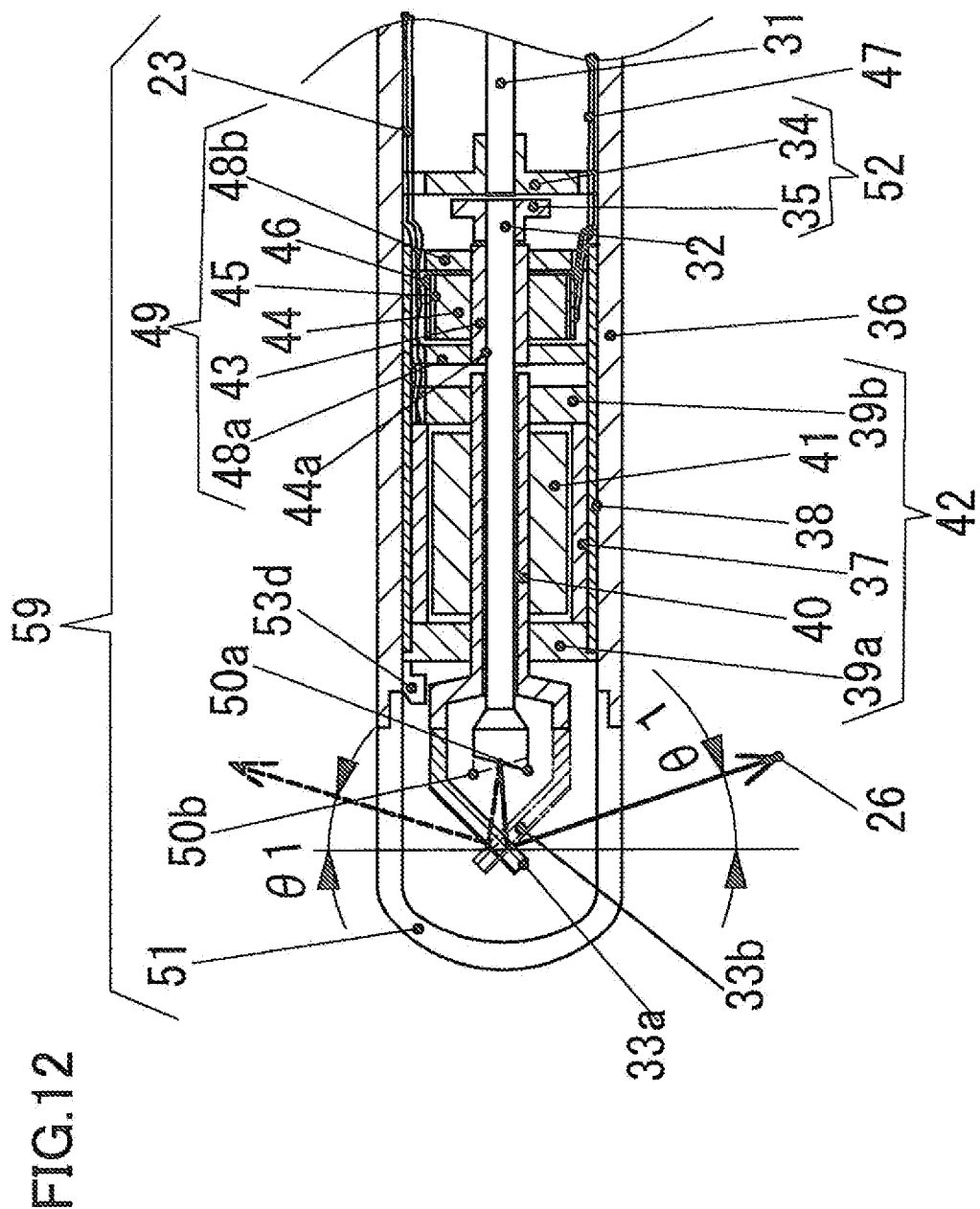
FIG. 12 is a cross-sectional view of a probe unit of an optical inner surface measuring device according to a second embodiment of the present invention.

FIG. 12 is a cross-sectional view of an optical inner surface measuring device according to the second embodiment of the present invention. A fixation-side optical fiber 31 is inserted into a sufficiently long hole of a tube 36 to guide a light ray from the back end side to the front end side of a probe 59, and is fixed by an optical fiber fixture 34.

A rotation-side optical fiber 32 is rotatably provided at the leading end side of the fixation-side optical fiber 31. First light path conversion units 33a and 33b formed from almost flat mirrors or the like are rotatably attached to the leading end of the rotation-side optical fiber 32 independently from the rotation-side optical fiber 32 by a first motor 42, and are configured to rotate and radiate a light ray in 360 degrees.

A second light path conversion unit 50 is attached to the leading end of the rotation-side optical fiber 32 to collect the light ray having passed through the fixation-side optical fiber 1 and rotate and radiate the light ray to the first light path conversion units 33a and 33b at a slight angle relative to the leading end direction.

The rotation-side optical fiber 32 and the fixation-side optical fiber 31 are opposed to each other with a very short distance of about 5 μm therebetween. The rotation-side optical fiber 32 and the fixation-side optical fiber 31 constitute a rotational optical connector 52 including a rotational light-shielding plate 35 and the optical fiber fixture 34. Accordingly, the rotation-side optical fiber 32 and the fixation-side optical fiber 31 are optically connected with little loss at a high light transmission rate maintained therebetween.

In the first motor 42, a motor coil 37 and first bearings 39a and 39b are fixed to a motor case 38, and a first hollow rotation shaft 40 with a rotor magnet 41 is rotated. A voltage is applied to the motor coil 37 by an electric wire 23. A first light path conversion unit 33 is attached to the first hollow rotation shaft 40.

In a second motor 49, second bearings 48a and 48b are attached to the motor case 38 to support rotatably a second rotation shaft 43, as in the first motor 42. Referring to FIG. 12, the second rotation shaft 43 is slightly pushed into a hole 44a at the almost center of a vibrator 44. The vibrator 44 has a spring property to generate a stable frictional force between the vibrator 44 and the second rotation shaft 43.

An electrostrictive element or piezoelectric element 45 is attached to the outer periphery of the vibrator 44, and an electrode 46 is formed at the element. The electrode is wired by an electric wire 47 illustrated in FIG. 12 for voltage application. The vibrator 44 is held so as not to rotate relative to the second bearings 48a and 48b. The electric wire 47 may simply perform the function of rotation blocking.

Referring to FIG. 12, a light passage unit 51 permeable to a light ray is attached to the tube 36 in the vicinity of the outer periphery of the first light path conversion unit 33 to which the light ray is radiated. The inner peripheral surface or outer peripheral surface of the light passage unit 51 has as appropriate a coating or the like to reduce surface reflection and increase light ray transmission.

The first motor 42 illustrated in FIG. 12 is rotationally driven with power supply from the first motor driver circuit 86 illustrated in FIG. 1, and the second motor 49 is rotationally driven with voltage application from the second motor driver circuit 87.

The first light path conversion unit 33 is formed from a rotatable mirror or prism that allows high-precision accuracy measurement with higher reflection efficiency and lower optical loss.

The second light path conversion unit 50 is formed from a prism having an almost flat inclined plane at the leading end that allows high-precision accuracy measurement with high light collection efficiency and reduced optical loss.

Next, characteristic operations and advantages of the foregoing three-dimensional scan-type optical imaging probe illustrated in FIGS. 12 to 16 will be described in detail.

A light ray such as a near infrared ray or a laser emitted from a light source in the measuring machine main body 85 illustrated in FIG. 1 passes through the fixation-side optical fiber 31 built into the tube 36.

Figure 14:
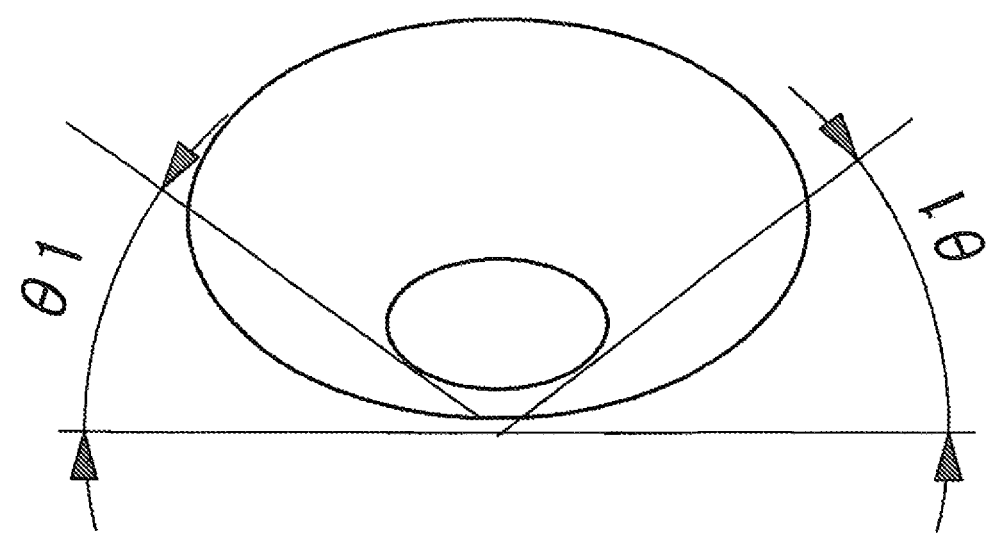
FIG. 14 is a diagram describing a scan angle of the optical inner surface measuring device.

Referring to FIG. 12, when the first motor 42 and the second motor 49 rotate at the same speed within the range between about 1800 to 20000 rpm with power supply from the electric wire 23, the guided light ray passes through the rotational optical connector 52 and the rotation-side optical fiber 32, and is emitted from a second light path conversion unit 50a. Then, the light ray is reflected on the almost flat plane portion of the first light path conversion unit 33a and is rotationally radiated with a change to a constant angular direction (at the angle θ1 in FIG. 12). The radiation range at that time has an umbrella shape formed by the angle θ1 as illustrated in FIG. 14.

The light ray such as a near infrared ray further passes through the light passage unit 51, and then is guided from the light passage unit 51, through the first light path conversion unit 33a, the second light path conversion unit 50a, the rotation-side optical fiber 32, the rotational optical connector 52, the fixation-side optical fiber 31, to the optical interference analysis unit 88, following the same light path as described above in the reverse direction.

Figure 13:
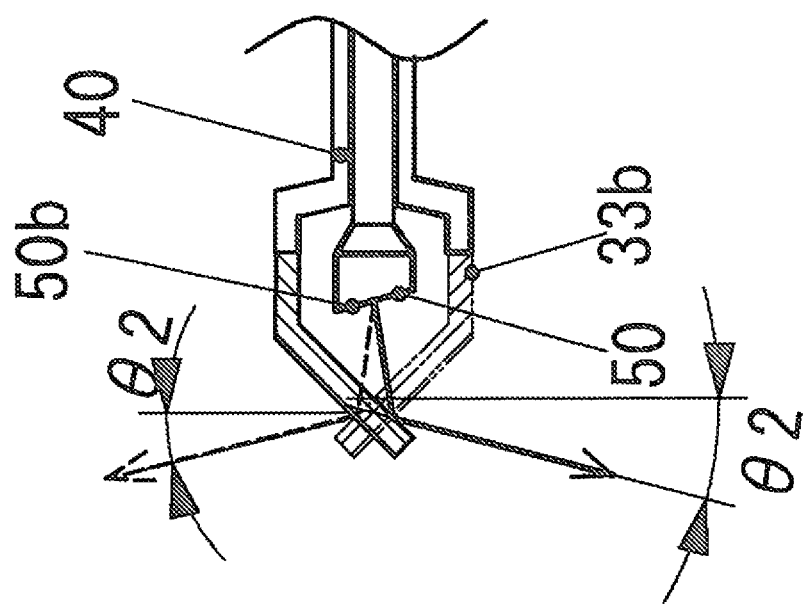
FIG. 13 is a diagram describing a three-dimensional scanning method of the optical inner surface measuring device.
Figure 15:
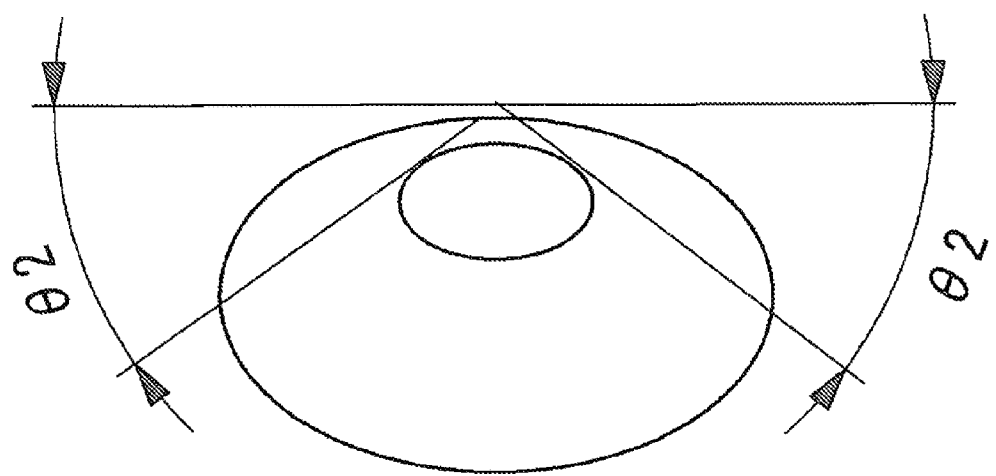
FIG. 15 is a diagram describing a scan angle of the optical inner surface measuring device.

Next, the rotation states of the first motor 42 and the second motor 49 are switched such that the first motor 42 rotates at a constant speed of 3600 rpm and the second motor 49 rotates at a constant speed of 3570 rpm, for example, with a slight difference in speed between the two motors. In this state, the first light path conversion unit 33 and the second light path conversion unit are gradually changed in rotation angle phase toward a position 50b. When a phase difference of 180 degrees is produced, the light ray is reflected on the rotating first light path conversion unit 33b so that the course of the light ray is changed at a constant angle to reach θ2 as illustrated in FIG. 13. The radiation range of the light ray at that moment is changed to an inclined shape as illustrated in FIG. 15.

While the first motor 42 makes 3600 revolutions per minute, the rotation phase angle is shifted by a difference in speed from the second motor 49, that is, by 30 revolutions. Accordingly, there is caused a difference in rotation phase of 360 degrees after each two seconds.

A runout detection sensor 53a detects outer periphery runout of the first hollow rotation shaft, and makes a modification to the collected original waveform data, as in the case of the example 1 illustrated in FIG. 5. Otherwise, another displacement detection unit for measuring the amount of runout of the rotation shaft unit of the first motor 42 detects a difference between the reference shape data on the inner periphery of the tube 6 stored in advance in a memory and the measurement data on the tube inner peripheral surface obtained during rotation of the first motor, as the amount of runout.

Figure 16:
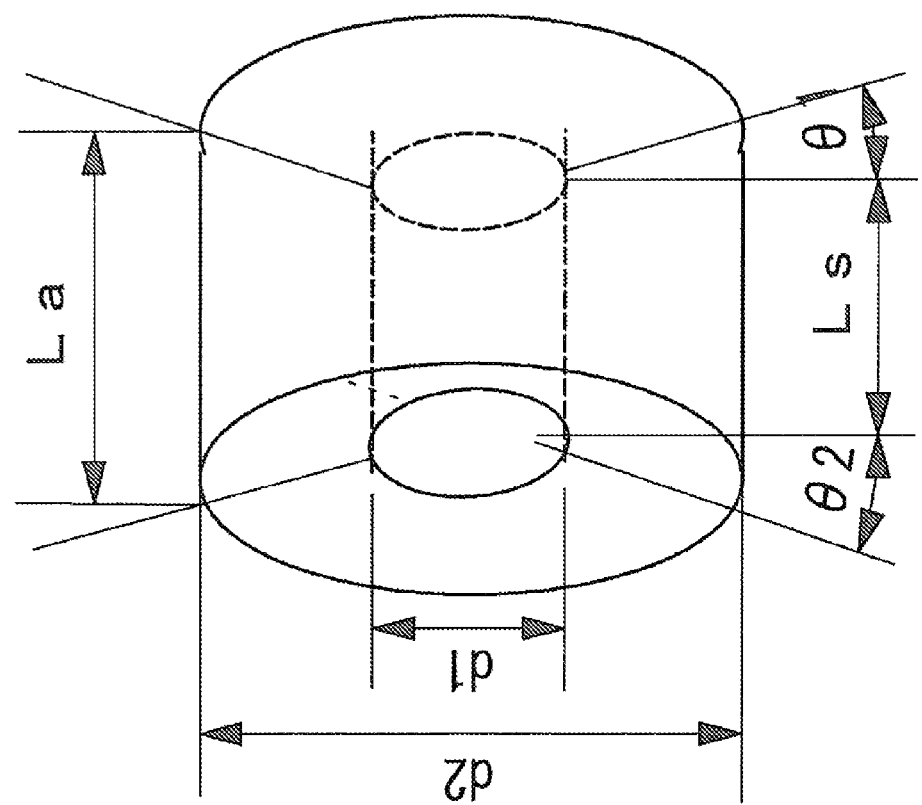
FIG. 16 is a diagram describing a three-dimensional scan range of the optical inner surface measuring device.

Successively, a rotation phase difference between the first light path conversion unit 33 and the second light path conversion unit 50 is slightly caused by one revolution after each two seconds. This operation changes continuously the radiation direction of the light ray within the range of θ1 to θ2. The light ray is repeatedly radiated in a three-dimensional manner within the range of θ1+θ2 as illustrated in FIG. 16. The signal line or the electric wires 23 and 47 do not exist within the scan range, which makes it possible to obtain clear three-dimensional image data without loss.

EXAMPLE 3

Figure 17:
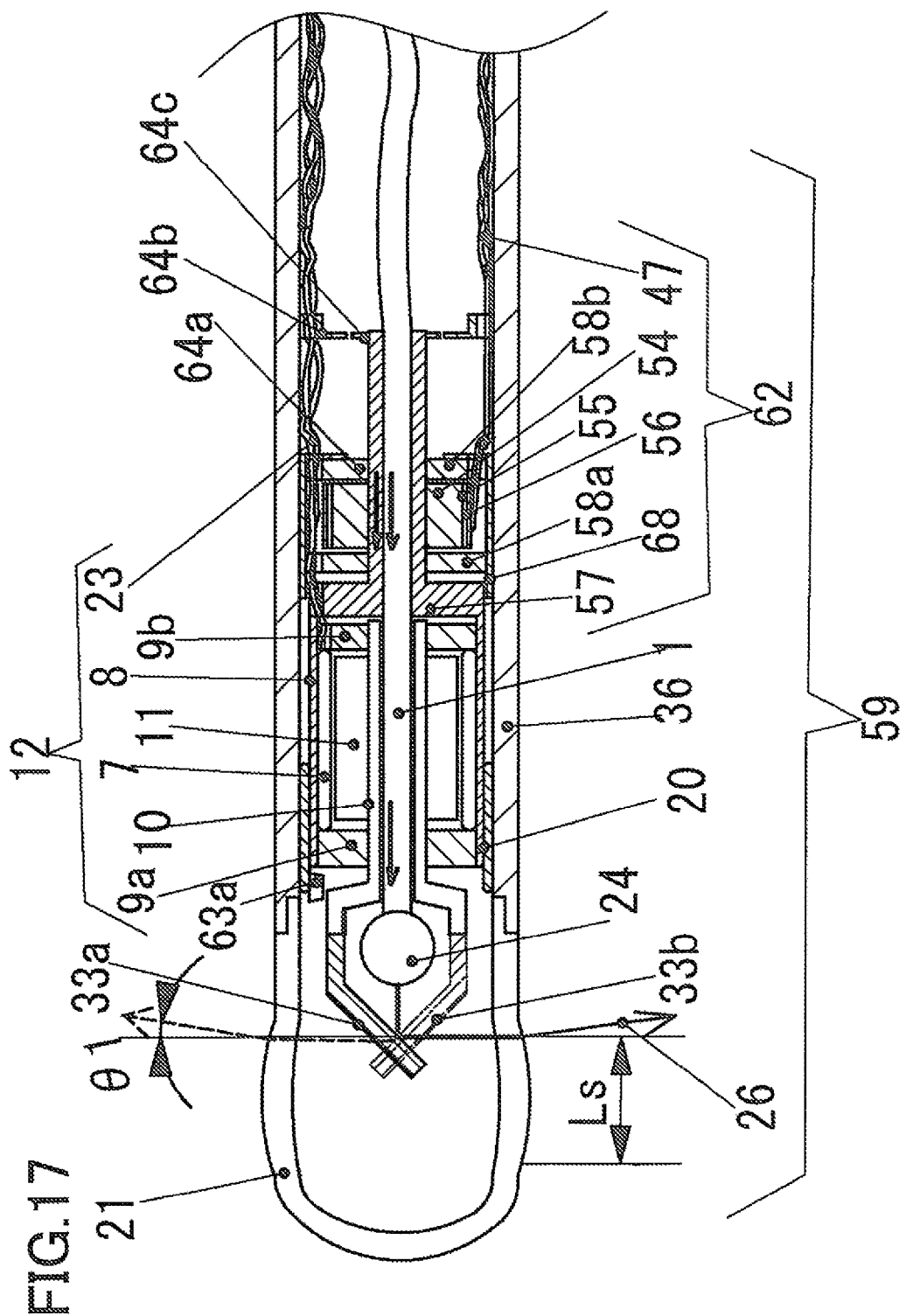
FIG. 17 is a cross-sectional view of a probe unit of an optical inner surface measuring device according to a third embodiment of the present invention.
Figure 18:
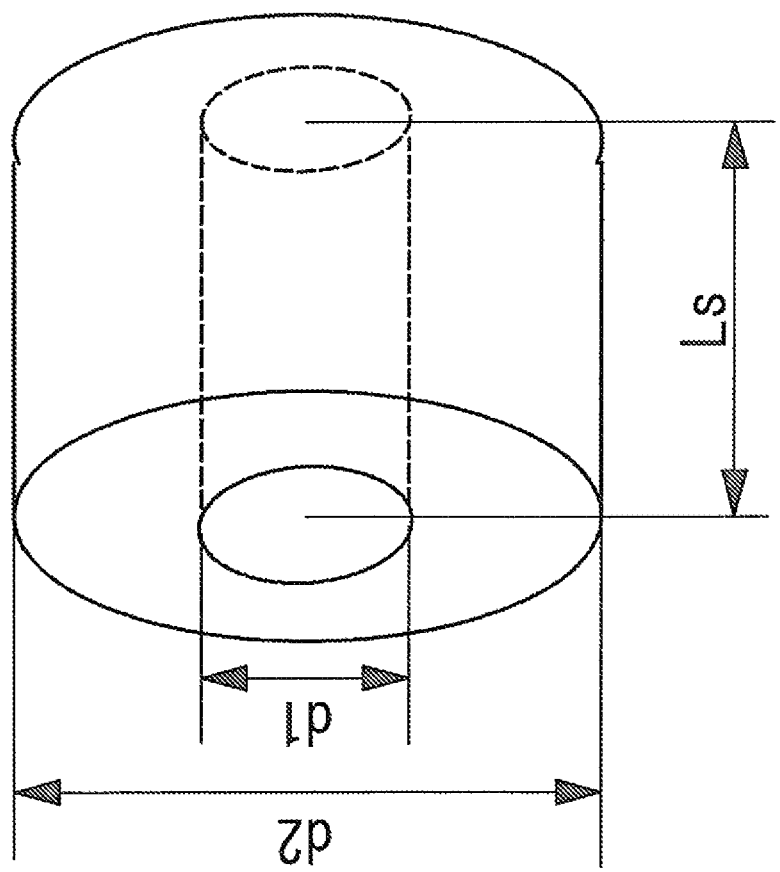
FIG. 18 is a diagram describing a three-dimensional scan range of the optical inner surface measuring device.

FIGS. 17 and 18 illustrate a third embodiment of an optical inner surface measuring device according to the present invention.

FIG. 17 is a cross-sectional view of the optical inner surface measuring device according to the embodiment of the present invention. The fixation-side optical fiber 1 is configured to transfer light between the leading end side (toward the light transmission member 21) and back end side of the probe 59. The fixation-side optical fiber 1 is built into the tube 36, and includes the light-collecting lens 24 such as a ball lens, for example, at the leading end side.

The first light path conversion unit 33 such as a rotational mirror with an inclined angle is provided at the leading end side of the light-collecting lens 24. The first motor 12 is rotated with voltage application from the electric wire 23.

The first motor 12 includes the first hollow rotation shaft 10 supported by the bearings 9a and 9b, in which the motor coil 7 is incorporated into the slidable motor case 8 supported by the slide guide 20 fixed to the inner peripheral surface of the tube 6.

In the first hollow rotation shaft 10, the rotor magnet 11 is fixed and the first light path conversion unit 33 is integrally provided.

A slide second shaft 57 is integrally provided behind the slidable motor case 8 on an almost central axis. The slide second shaft 57 is a hollow shaft and the fixation-side optical fiber 1 is inserted into the hollow and adhered and fixed to the slide second shaft 57.

In a direct-acting motor 62, sliding bearings 58a and 58b are provided in a motor case 68 within the tube 36 to support the slide second shaft 57, and are slightly pushed into a central hole of an almost polygonal column-shaped vibrator 54 on the outer periphery of the slide second shaft 57. A piezoelectric element 55 with a pattern electrode 56 is attached to at least the outer peripheral surface of the vibrator 54.

When a voltage from the electric wire 47 is applied to the pattern electrode 56, the piezoelectric element 55 starts to vibrate and causes a general-form or triangle-form traveling wave to the vibrator 54. Accordingly, the slide second shaft 57 slides axially the direct-acting motor 62, the fixation-side optical fiber 1, the light-collecting lens 24, and the first light path conversion unit 33 within the range of 5 to 30 mm, for example, as indicated with Ls in the drawing.

Referring to FIG. 17, the fixation-side optical fiber 1 built into the tube 36 is longer than the tube 36 by at least Ls mm or more, and is stored in a curved state in the tube 36 for a margin of length. Accordingly, referring to FIG. 17, when the direct-acting motor 62 operates to move the slide second shaft 57 and the first motor 12 in the tube 36 toward the leading end side, the fixation-side optical fiber 1 can be smoothly slid by a sufficient small force of pushing and pulling.

Next, characteristic operations and advantages of the foregoing optical inner surface measuring device illustrated in FIGS. 17 and 18 will be described in detail.

Referring to FIG. 17, when being powered by the electric wire 23, the motor coil 7 of the first motor 12 generates a rotating magnetic field to provide a rotational force to the rotor magnet 11. The first hollow rotation shaft 10 rotates the first light path conversion unit 33 at a constant speed within the range of 1800 to 10000 rpm.

The first light path conversion unit 33 is indicated as 33*a* at the rotation position and as 33*b* at a position rotated 180 degrees from the position 33*a*.

The infrared ray or laser light ray emitted from the measuring machine main body 85 illustrated in FIG. 1 is guided to the fixation-side optical fiber 1, emitted forward from the light-collecting lens 24, and then radiated at an almost right angle from the first light path conversion unit 33. The reflection light from the target object 61 is returned to the measuring machine main body 85 through the fixation-side optical fiber 1, which allows the measuring machine main body 85 to display an image.

The probe 59 illustrated in FIG. 17 corresponds to the probe 28 illustrated in FIG. 1. The tube 36 illustrated in FIG. 17 corresponds to the tube 6 illustrated in FIG. 1.

Referring to FIG. 17, when the pattern electrode 56 is powered through the electric wire 47, the piezoelectric element 55 generates a traveling wave to provide the slide second shaft 57 with a force of sliding toward the leading end side. Then, the slide second shaft 57 starts to move integrally with the first motor 12, the first light path conversion unit 33, the fixation-side optical fiber 1, and the light-collecting lens 24 to the leading end side. The light ray is radiated in 360 degrees at an almost right angle or in a direction indicated with θ1, and is slid in the axial direction at the same time. Accordingly, radiating the light ray three-dimensionally as illustrated in FIG. 18 allows the measuring machine main body 85 illustrated in FIG. 1 to collect and accumulate three-dimensional image data.

Referring to FIGS. 17 and 18, when the slide second shaft 57 moves by the distance of Ls illustrated in the drawing, a movement-side sensor 64*c* enters into proximity to a fixation-side sensor 64*a* and generates a signal indicative of completion of the sliding action. Accordingly, the application of a voltage from the electric wire 23 to the pattern electrode 56 is stopped. Otherwise, the way of voltage application is changed so that the slide second shaft 57 starts to move in the reverse direction.

A runout detection sensor 63*a* detects outer periphery runout of the first hollow rotation shaft, and makes a modification to the collected original waveform data, as in the case of the example 1 illustrated in FIG. 5. Otherwise, another displacement detection unit for measuring the amount of runout of the rotation shaft unit of the first motor 12 detects a difference between the reference shape data on the inner periphery of the tube 6 stored in advance in a memory and the measurement data on the tube inner peripheral surface obtained during rotation of the first motor, as the amount of runout.

In this example, the light-collecting lens 24 is a ball lens. Alternatively, the light-collecting lens 24 may be a conical light-collecting lens.

One of requisite performances for this kind of three-dimensional scanning inner surface observation and inspection device is to increase spatial resolution. Factors for achieving requisite spatial resolution include reducing variations in speed of the motor 12, and improving the accuracies of runout and non-repeatable runout of the first hollow rotation shaft 10, the accuracy of the first light path conversion element 33, the surface precision of the light-collecting lens 24, and the like.

Of the foregoing factors, the reduction of variations in speed of the motor 12 has the largest influence. This system in which the motor 12 is built into the leading end portion of the probe 59 achieves stably as a high three-dimensional spatial resolution as 1 μm or less, for example. In addition, the axial sliding action of the direct-acting actuator 22 allows a light ray to be axially radiated within a constant range to obtain a high-resolution three-dimensional observation image.

As described above, the optical inner surface measuring device of the present invention includes a means for detecting the amount of runout of the rotation shaft unit of the motor. In addition, shape data on the inner peripheral surface of the target object is obtained by calculating at a computer reflection light from the target object through the optical fiber, and is modified by displacement amount data from the displacement sensor. This realizes high-precision measurement with no error in the collected data on the inner peripheral surface of the target object resulting from runout and rotational vibration of the rotation shaft of the motor emitting the light ray for scanning

INDUSTRIAL APPLICABILITY

An optical inner diameter measuring device configured to observe and measure a target object using the interference optical method of the present invention is applicable to industrial diagnostic devices for high-precision measurement, and for example, three-dimensional observation of the bottom of a deep hole. The optical inner diameter measuring device is expected to be used for numerical diagnosis based on changes in dimension of a minute focus of disease and for medical treatment in the medical field.

What is claimed is:

1. An optical inner surface measuring device configured to observe and measure a target object using an interference optical method, comprising:
 a tube;
 an optical fiber built into the tube;
 at least one light path conversion unit arranged at a leading end side of the optical fiber;

a motor having a rotation shaft unit and configured to rotationally drive one or both of the optical fiber and the light path conversion unit; and a displacement detector configured to measure an amount of runout of the rotation shaft unit of the motor, wherein the displacement detector is provided by arranging at least one detection sensor in the tube and facing an outer peripheral surface of the rotation shaft unit, wherein the motor includes a first motor and a second motor arranged behind the first motor, the light path conversion unit includes a first light path conversion unit operated by the first motor and a second light path conversion unit operated by the second motor, the optical fiber includes a fixation-side optical fiber arranged non-rotatably in the tube via a fixture behind the second motor and a rotation-side optical fiber rotating integrally with the rotation shaft unit of the first motor or the second motor, each of the rotation shaft units of the first motor and the second motor has a hollow shape, at least part of the rotation-side optical fiber at the leading end side is inserted into the hollow of the rotation shaft unit of the first motor, and at least part of the rotation-side optical fiber at a back side is fixed to the hollow of the rotation shaft unit of the second motor, the first light path conversion unit is arranged at the leading end side of the second light path conversion unit so as to be rotatable integrally with the rotation shaft unit of the first motor, and the second light path conversion unit is provided at the leading end of the rotation-side optical fiber.

2. The optical inner surface measuring device according to claim 1, wherein reflection light from the target object obtained through the optical fiber is modified based on shape data on an inner peripheral surface of the target object obtained by calculation at a computer and displacement amount data from the displacement detector.

3. The optical inner surface measuring device according to claim 1, wherein the displacement detector detects, as the amount of runout, a difference between reference shape data on an inner peripheral surface or outer peripheral surface of the tube and measurement data on the inner peripheral surface or outer peripheral surface of the tube obtained during rotation of the rotation shaft unit.

4. The optical inner surface measuring device according to claim 1, wherein a bearing supporting the rotation shaft unit of at least one of the first and second motors is a dynamic-pressure bearing with a dynamic-pressure groove.

5. The optical inner surface measuring device according to claim 1, wherein
the light path conversion unit is arranged so as to be rotatable integrally with the rotation shaft unit of at least one of the first and second motors, and
the optical fiber is inserted into a hollow of the rotation shaft unit of the at least one of the first and second motors so as to be rotatable relative to the rotation shaft unit.

6. An optical inner surface measuring device configured to observe and measure a target object using an interference optical method, comprising:

an optical fiber built into a tube; at least one light path conversion unit arranged at a leading end side of the optical fiber;

a motor configured to rotationally drive one or both of the optical fiber and the light path conversion unit; and a displacement detector configured to measure an amount of runout of a rotation shaft unit of the motor, wherein the motor includes a first motor and a second motor arranged behind the first motor, the light path conversion unit includes a first light path conversion unit operated by the first motor and a second light path conversion unit operated by the second motor, the optical fiber includes a fixation-side optical fiber arranged non-rotatably in the tube via a fixture behind the second motor and a rotation-side optical fiber rotating integrally with the rotation shaft unit of the first motor or the second motor, each of the rotation shaft units of the first motor and the second motor has a hollow shape, at least part of the rotation-side optical fiber at the leading end side is inserted into the hollow of the rotation shaft unit of the first motor, and at least part of the rotation-side optical fiber at a back side is fixed to the hollow of the rotation shaft unit of the second motor, the first light path conversion unit is arranged at the leading end side of the second light path conversion unit so as to be rotatable integrally with the rotation shaft unit of the first motor, and the second light path conversion unit is provided at the leading end of the rotation-side optical fiber.

7. The optical inner surface measuring device according to claim 6, wherein the first light path conversion unit is a rotatable mirror or prism.

8. The optical inner surface measuring device according to claim 6, wherein the second light path conversion unit is a prism with an almost flat plane inclined toward the leading end.

* * * * *